United States Patent
Knowles et al.

(10) Patent No.: US 6,855,669 B2
(45) Date of Patent: Feb. 15, 2005

(54) USE OF α,β UNSATURATED ALIPHATIC ALDEHYDES AND KETONES TO INHIBIT POTATO TUBER SPROUTING

(75) Inventors: Norman R. Knowles, Pullman, WA (US); Lisa O'Rear Knowles, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 10/450,233

(22) PCT Filed: Dec. 13, 2001

(86) PCT No.: PCT/US01/48907

§ 371 (c)(1),
(2), (4) Date: Sep. 19, 2003

(87) PCT Pub. No.: WO02/058464

PCT Pub. Date: Aug. 1, 2002

(65) Prior Publication Data

US 2004/0053787 A1 Mar. 18, 2004

Related U.S. Application Data

(60) Provisional application No. 60/301,862, filed on Jun. 29, 2001, and provisional application No. 60/255,996, filed on Dec. 14, 2000.

(51) Int. Cl.$^7$ .............................................. A01N 35/02
(52) U.S. Cl. ..................................................... 504/348
(58) Field of Search ........................................ 504/348

(56) References Cited

U.S. PATENT DOCUMENTS

| | | |
|---|---|---|
| 4,336,273 A | 6/1982 | Lee |
| 5,129,951 A | 7/1992 | Vaughn et al. |
| 5,139,562 A | 8/1992 | Vaughn et al. |
| 5,436,226 A | 7/1995 | Lulai et al. |
| 5,580,596 A | 12/1996 | Winkelmann et al. |

OTHER PUBLICATIONS

Agelopoulos, N.G., et al., "A Novel Approach for Isolation of Volatile Chemicals Released by Individual Leaves of a Plant In Situ," *J. Chem. Ecol.* 25(6):1411–1425, 1999.

Archbold, D.D., et al., "Fumigating 'Crimson Seedless' Table Grapes With (E)–2–Hexenal Reduces Mold During Long–Term Postharvest Storage," *HortScience* 34(4):705–707, 1999.

Corbo, M.R., et al., "Effects of Hexanal, trans–2–Hexenal, and Storage Temperature on Shelf Life of Fresh Sliced Apples," *J. Agric. Food Chem.* 48:2401–2408, 2000.

Deng, W., et al., "Effects of Six–Carbon Aldehydes and Alcohols on Bacterial Proliferation," *J. Agric. Food Chem.* 41:506–510, 1993.

(List continued on next page.)

*Primary Examiner*—S. Mark Clardy
(74) *Attorney, Agent, or Firm*—Christensen, O'Connor, Johnson Kindness PLLC

(57) ABSTRACT

The present invention provides methods for inhibiting sprouting of potato tubers, the methods each including the step of contacting a potato tuber with an amount of a chemical agent including at least one aliphatic carbonyl compound selected from the group consisting of a $C_3$ to $C_{14}$, α,β unsaturated aliphatic aldehyde and a $C_4$ to $C_{14}$, α,β unsaturated aliphatic ketone, wherein the amount of the chemical agent is effective to inhibit potato tuber sprouting. Some aldehydes and ketones useful in the practice of the present invention are defined by formulae I and II, respectively, as set forth herein. In the practice of the methods of the invention the chemical agent is applied after the potato tubers have been harvested, but typically not later than the onset of sprouting.

35 Claims, 6 Drawing Sheets

OTHER PUBLICATIONS

Hartmans, K.J., et al., "The Use of Carvone in Agriculture: Sprout Suppression of Potatoes and Antifungal Activity Against Potato Tuber and Other Plant Diseases," *Industrial Crops and Products* 4:3–13, 1995.

Major, R.T., et al., "Isolation From *Ginkgo biloba* L. of an Inhibitor of Fungus Growth," *J. Biol. Chem.* 235(11):3298–3299, 1960.

Riley, J.C.M., and J.E. Thomson, "Ripening–Induced Acceleration of Volatile Aldehyde Generation Following Tissue Disruption in Tomato Fruit," *Physiol. Plant.* 104:571–576, 1998.

Vokou, D., et al., "Effects of Aromatic Plants on Potato Storage: Sprout Suppression and Antimicrobial Activity," *Agric. Ecosyst. Environ.* 47:223–235, 1993.

USE OF α,β UNSATURATED ALIPHATIC ALDEHYDES AND KETONES TO INHIBIT POTATO TUBER SPROUTING

This application has been filed under 35 USC 371 as the national stage of international application PCT/US01/48907, filed Dec. 13, 2001, which claims benefit of Ser. No. 60/255,996, filed Dec. 14, 2000, and claims benefit of Ser. No. 60/301,862 filed Jun. 29, 2001.

FIELD OF THE INVENTION

This invention relates to the use of α,β unsaturated aliphatic aldehydes and ketones to inhibit sprouting of potato tubers.

BACKGROUND OF THE INVENTION

Potatoes destined for storage are subjected to wound healing immediately following harvest, during the initial phase of the storage season. During this period, wound periderm develops over cuts and abrasions that resulted from mechanical injury during harvesting. The healing period allows for optimal skin set and suberization of cut surfaces, ultimately providing a barrier against water loss and bacterial and fungal infection. In general, the rate of wound healing is dependent upon temperature; healing occurring faster at higher temperatures. However, high temperature at the beginning of storage often stimulates pathogens and influences various physiological processes (e.g., respiration) that can lead to reduced storability for seed potatoes, fresh market potatoes and processing potatoes. Hence, the temperature selected for wound healing is usually a compromise. Holding tubers at 10° C. to 15° C. for ten to fourteen days under high humidity stimulates periderm development and suberization while minimizing the potential for tuber decay.

Storage temperature is lowered to holding levels after the healing period. The holding temperature depends on the market for which the tubers are destined. Fresh market tubers can be held at 4° C., as cold-induced sweetening is not a concern. This low temperature stimulates reducing sugar accumulation, effects a relatively long dormant period, and results in the longest storage life. Nonetheless, potato tubers destined for purchase by consumers are often treated with a chemical sprout inhibitor early in the storage season, and may receive another treatment of sprout inhibitor before being bagged ready for shipment to retail outlets.

Potatoes that will be processed to make french fries or potato chips (i.e., processing potatoes) must be held at higher temperatures (around 10° C.) to prevent buildup of reducing sugars. Accumulation of reducing sugars during storage at low temperatures reduces the quality of processed potato products. In particular, heating during the deep-frying process induces a non-enzymatic reaction between reducing sugars and amino acids, giving an undesirable color, flavor and texture to the processed product. Hence, buildup of sugars in potatoes stored at low temperature is a major problem for processors. Cold-induced sweetening is avoided over the short term by storing tubers at a higher temperature (around 10° C.); however, in the absence of chemical sprout inhibitors, the ultimate storage life is greatly reduced by loss of dormancy and early sprouting stimulated by the higher temperature. Thus, virtually all processing potatoes are treated with chemical sprout inhibitors.

Sweetening in stored processing potatoes can be at least partially reversed by a reconditioning process in which potato tubers are stored for a one to three week period at a higher temperature of about 15° C. before being processed. The higher storage temperature stimulates respiration and the degradation of reducing sugars in the tubers. Higher storage temperature, especially when applied toward the end of the natural dormancy period of potato tubers, promotes sprouting, and so sprout inhibitors are typically applied during the reconditioning process.

The main sprout inhibitors registered for use on potatoes are chlorpropham (CIPC), maleic hydrazide (MH), and dimethylnaphthalene (DMN). Diisopropylnaphthalene (DIPN) has received an experimental use permit to be used in combination with CIPC. The two chemicals in combination (CIPC plus DIPN) appear to be more effective at lower concentrations than either of the two chemicals alone.

The United States Environmental Protection Agency (EPA) considers CIPC as a group E chemical (evidence for non-carcinogenicity for humans). CIPC was originally registered in the U.S. as a pre- and post-emergence herbicide in 1962 and the EPA has set residue limits for potato tubers. Notwithstanding the safety record of CIPC, the trend today is to reduce the use of synthetic pesticides in agriculture, and thus reduce chemical residues in the global food supply. CIPC is continually being scrutinized by the EPA as it is among the three pesticides found in the highest concentrations in the average American diet (Gartrell et al., *J. Assoc. Off. Anal. Chem.* 69:146–161 (1986)).

A need therefore exists for methods to inhibit potato tuber sprouting that utilize environmentally benign chemicals, such as natural phytochemicals.

SUMMARY OF THE INVENTION

In accordance with the foregoing, the present invention provides methods for inhibiting sprouting of potato tubers, the methods each including the step of contacting a potato tuber with an amount of a chemical agent including at least one aliphatic carbonyl compound selected from the group consisting of a $C_3$ to $C_{14}$, α,β unsaturated aliphatic aldehyde and a $C_4$ to $C_{14}$, α,β unsaturated aliphatic ketone, wherein the amount of the chemical agent is effective to inhibit potato tuber sprouting. Some aldehydes and ketones useful in the practice of the present invention are defined by formulae I and II, respectively, as set forth herein. Typically, the chemical agent is applied simultaneously, or substantially simultaneously, to numerous, harvested, potato tubers. In the practice of the methods of the invention the chemical agent is applied after the potato tubers have been harvested, but typically not later than the onset of sprouting. In some embodiments of the methods of the invention, the amount of chemical agent is sufficient to provide a dosage of the at least one aliphatic carbonyl compound of from 0.001 mmol/kg potato tubers to 100 mmol/kg potato tubers.

The methods of the invention are useful for inhibiting sprouting of potato tubers in any situation in which sprouting inhibition is desired. For example, the methods of the invention are useful for inhibiting sprouting of potato tubers that are stored before being sold to consumers, or to processors for making french fries or potato chips.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1A:
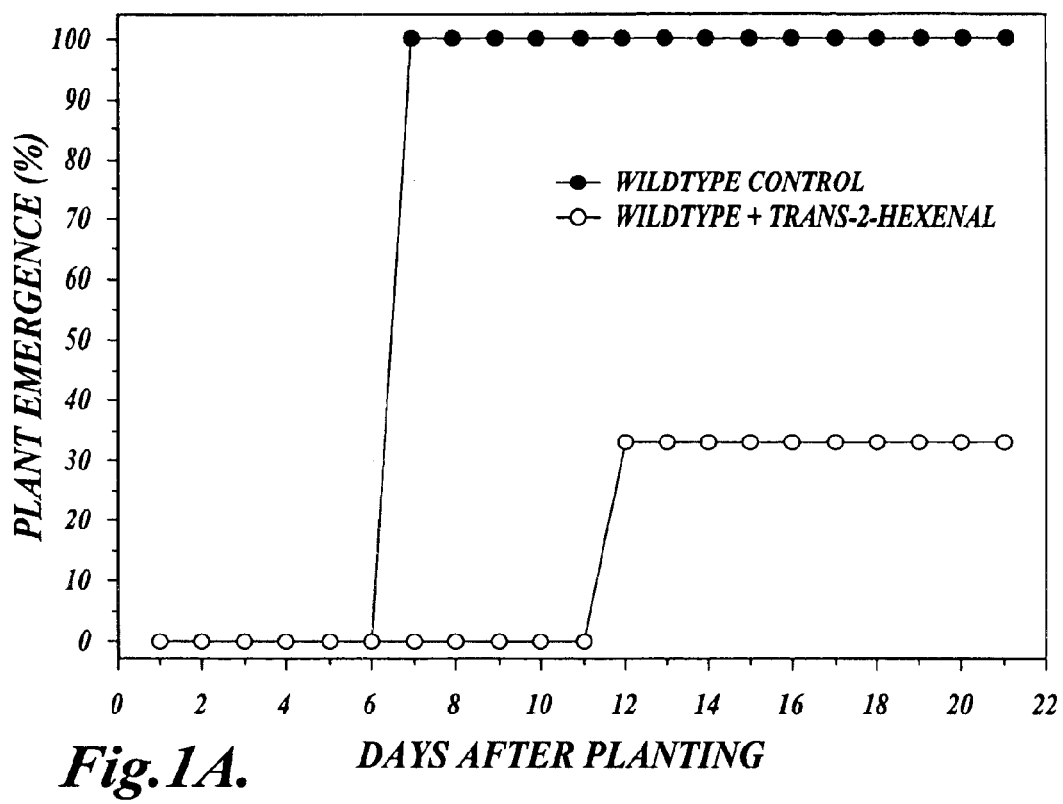
FIG. 1A shows the percentage of plant emergence from potato tubers treated with trans-2-hexenal (open circles), and from potato tubers that were not treated with trans-2-hexenal (filled circles).
Figure 1B:
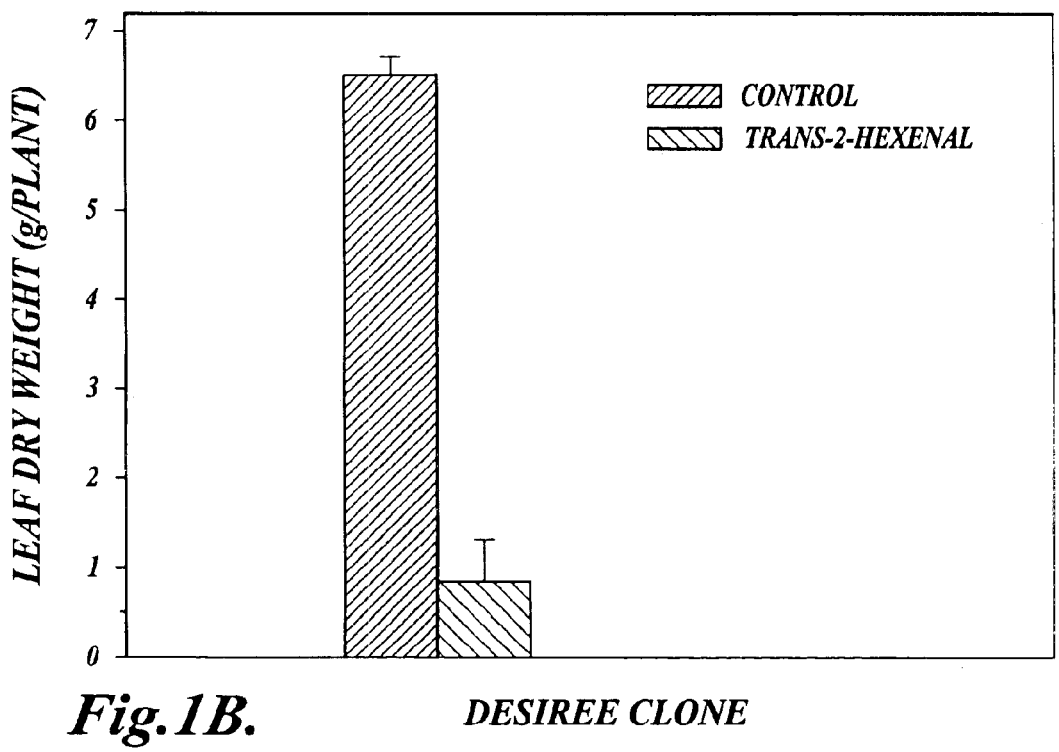
FIG. 1B shows the effect of trans-2-hexenal on leaf dry weight of potato plants germinated from potato tubers treated with trans-2-hexenal.
Figure 1C:
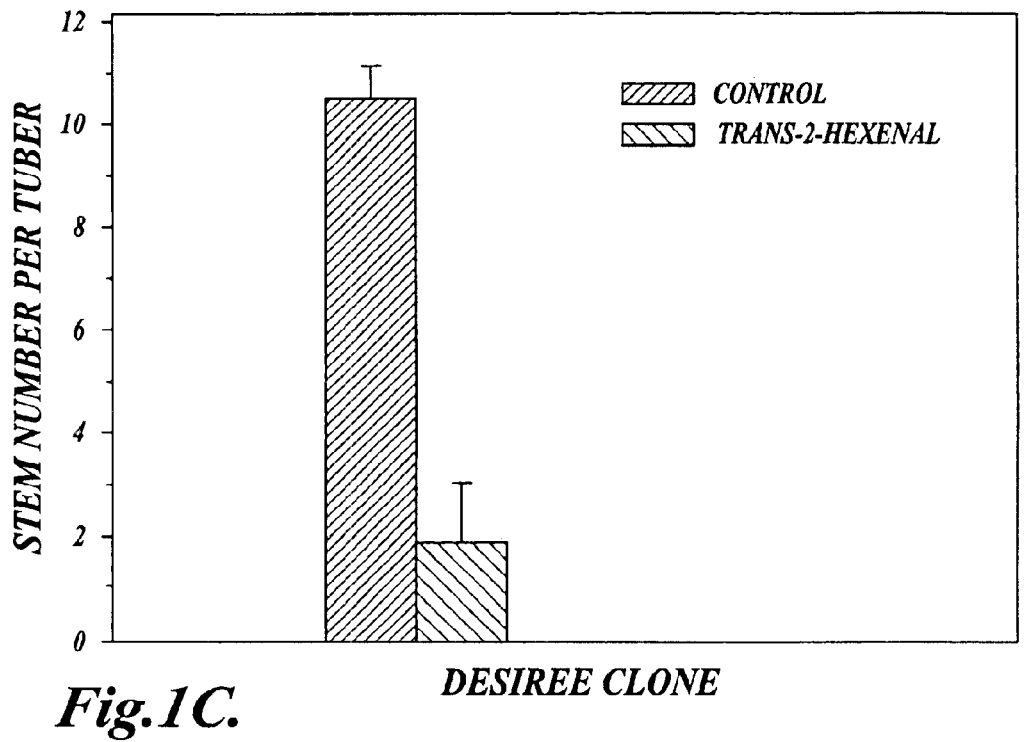
FIG. 1C shows the effect of trans-2-hexenal on the number of stems growing from potato tubers treated with trans-2-hexenal.
Figure 1D:
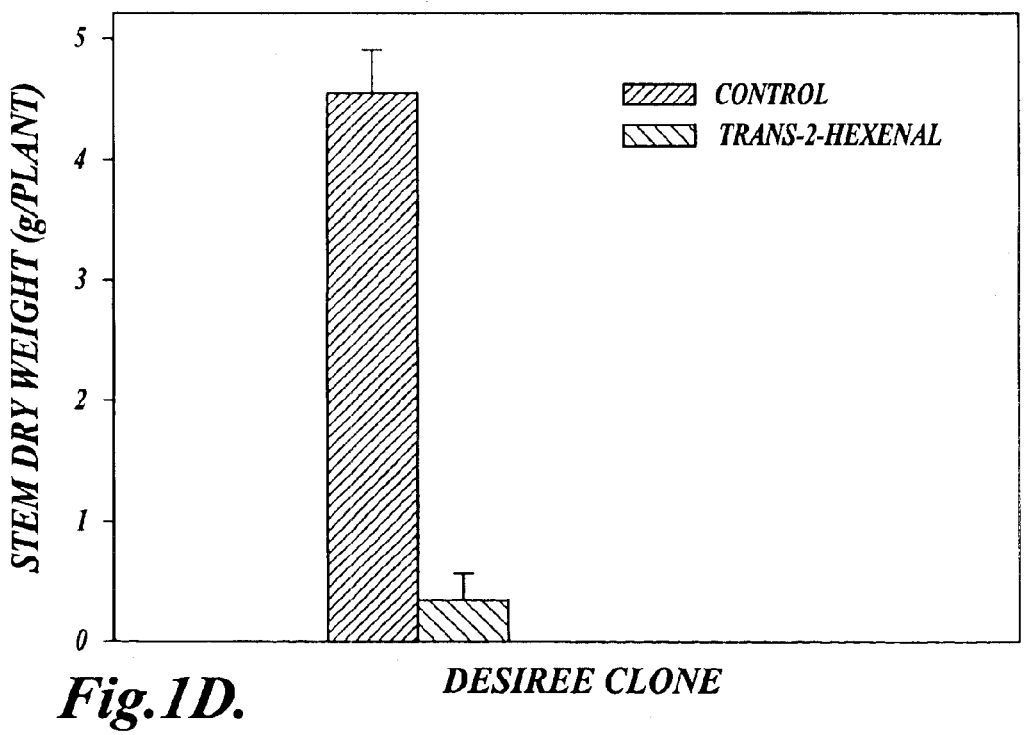
FIG. 1D shows the effect of trans-2-hexenal on stem dry weight of potato plants germinated from potato tubers treated with trans-2-hexenal.
Figure 1E:
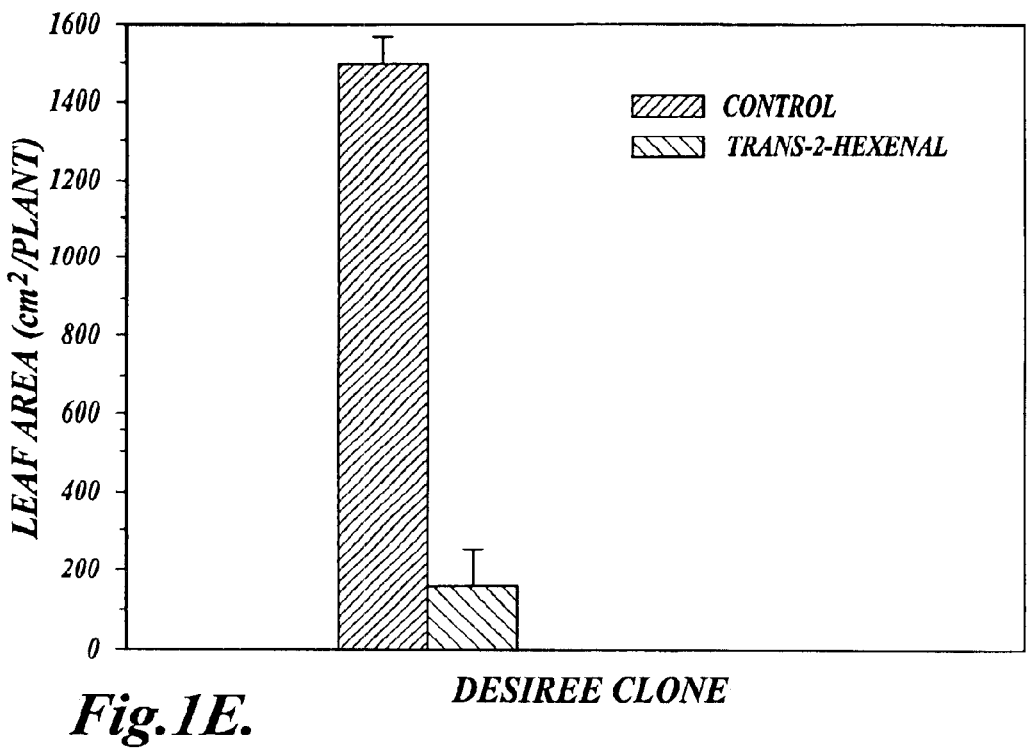
FIG. 1E shows the effect of trans-2-hexenal on leaf area of potato plants germinated from potato tubers treated with trans-2-hexenal.
Figure 1F:
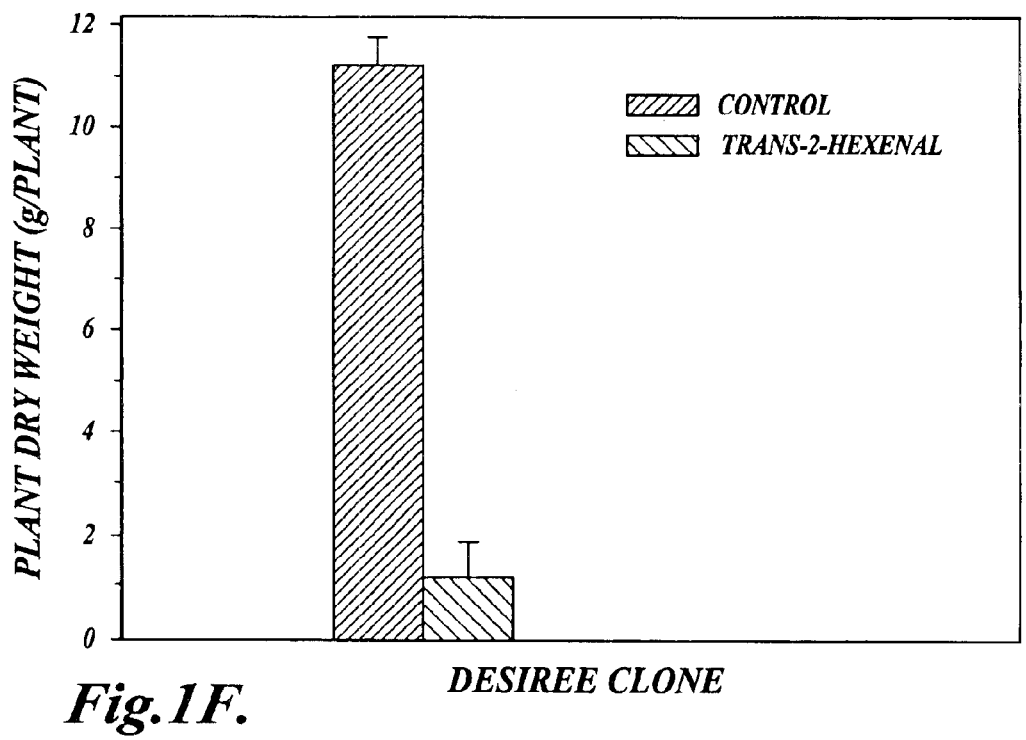
FIG. 1F shows the effect of trans-2-hexenal on plant dry weight of potato plants germinated from potato tubers treated with trans-2-hexenal.
Figure 2B:
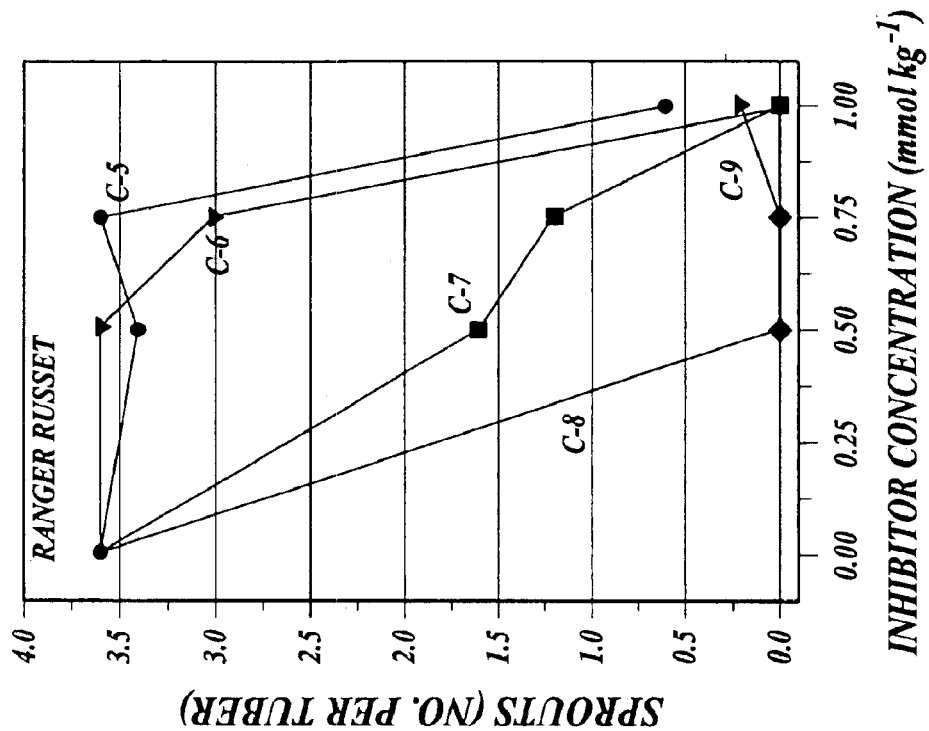
FIG. 2B shows the effects of trans-2-pentenal, (C-5), trans-2-hexenal (C-6), trans-2-heptenal (C-7), trans-2-octenal (C-8) and trans-2-nonenal (C-9) on the number of sprouts that grew from Ranger Russet potato tubers following storage at 8° C. (46° F.), 95% relative humidity (RH), for 17 weeks. The tubers were treated as described in the legend to FIG. 2A, and in Example 5.
Figure 2A:
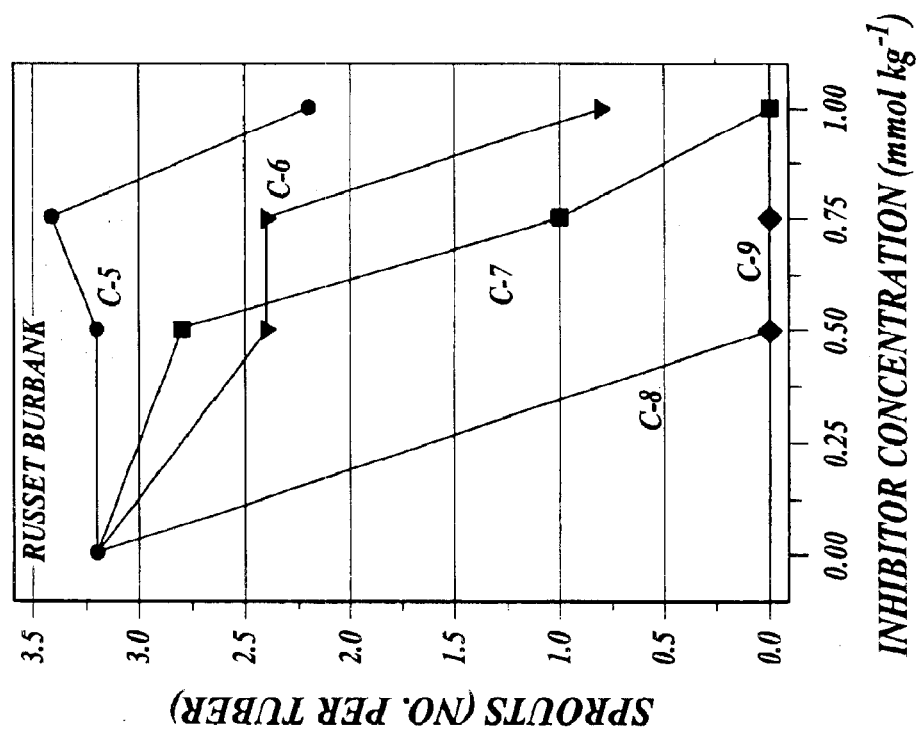
FIG. 2A shows the effects of trans-2-pentenal, (C-5), trans-2-hexenal (C-6), trans-2-heptenal (C-7), trans-2-octenal (C-8) and trans-2-nonenal (C-9) on the number of sprouts that grew from Russet Burbank potato tubers following storage at 8° C. (46° F.), 95% relative humidity (RH), for 17 weeks. As described more fully in Example 5, four-month-old tubers (previously stored at 4° C.) were treated (for 24 h) with different concentrations of the aldehydes in mid January. The treated tubers were then stored in the dark for 120 days (17 weeks).
Figure 2D:
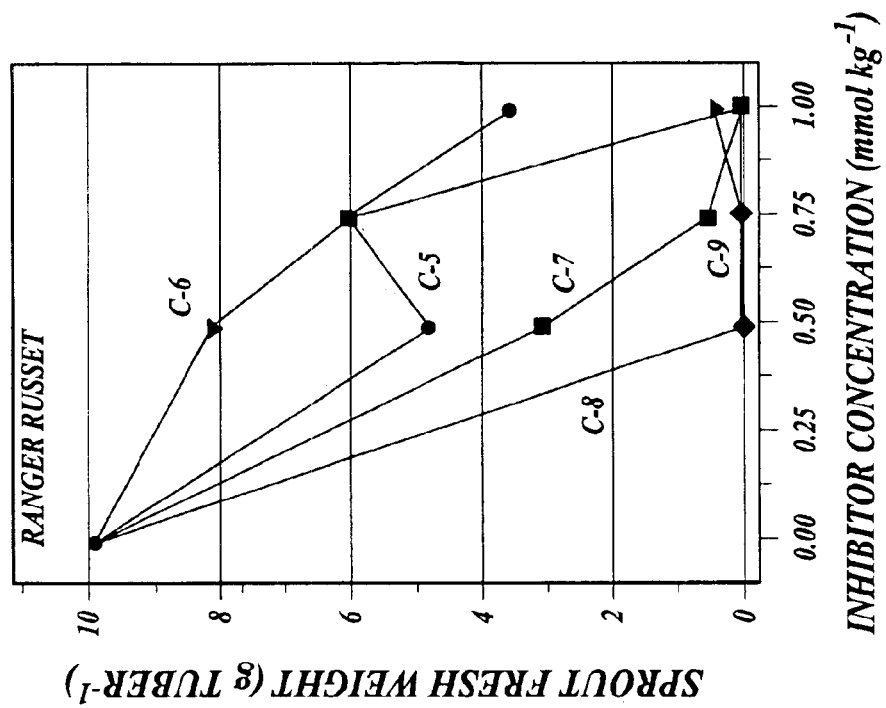
FIG. 2D shows the effects of trans-2-pentenal, (C-5), trans-2-hexenal (C-6), trans-2-heptenal (C-7), trans-2-octenal (C-8) and trans-2-nonenal (C-9) on the fresh weight of sprouts that grew from Ranger Russet potato tubers following storage at 8° C. (46° F.), 95% relative humidity (RH), for 17 weeks. The tubers were treated as described in the legend to FIG. 2A, and in Example 5.
Figure 2C:
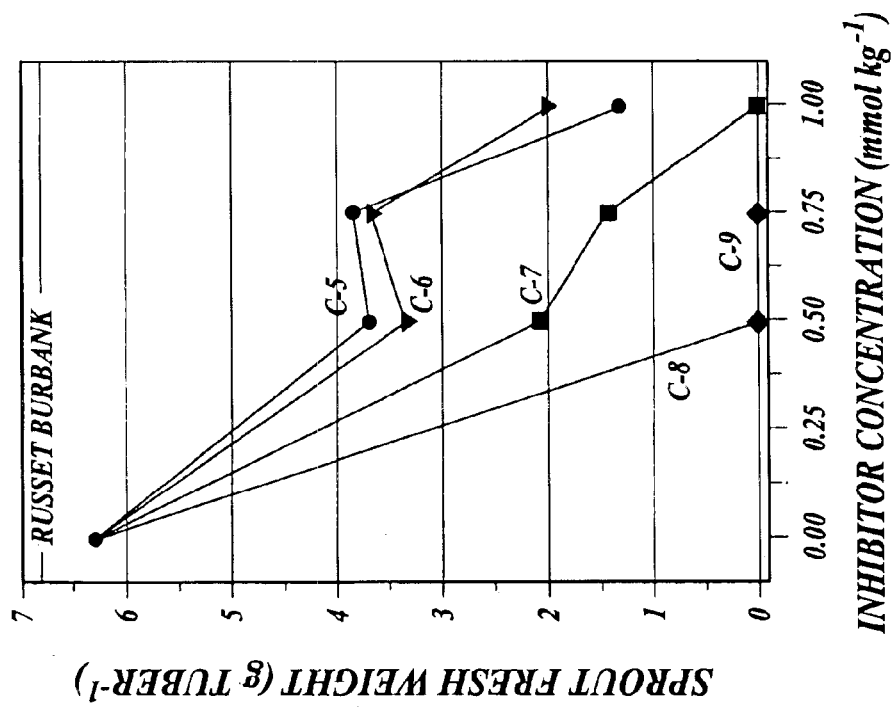
FIG. 2C shows the effects of trans-2-pentenal, (C-5), trans-2-hexenal (C-6), trans-2-heptenal (C-7), trans-2-octenal (C-8) and trans-2-nonenal (C-9) on the fresh weight of sprouts that grew from Russet Burbank potato tubers following storage at 8° C. (46° F.), 95% relative humidity (RH), for 17 weeks. As described more fully in Example 5, four-month-old tubers (previously stored at 4° C.) were treated (for 24 h) with different concentrations of the aldehydes in mid January. The treated tubers were then stored in the dark for 120 days (17 weeks).

Unless specifically defined herein, all terms used herein have the same meaning as they would to one skilled in the art of the present invention. U.S. provisional patent application serial No. 60/255,996, filed Dec. 14, 2000, and U.S. provisional patent application serial No. 60/301,862, filed Jun. 29, 2001, are both incorporated herein by reference in their entirety.

As used herein, the term "potato tuber" refers to the underground storage organ of the potato plant (*Solanum tuberosum*). The tuber is a modified stem and includes buds that can sprout and form new potato plants.

The phrase "effective to inhibit sprouting" means that: (a) the number, and/or the weight, of stems growing from a defined number of potato tubers contacted with a chemical agent in accordance with the present invention is less than the number, and/or the weight, of stems growing from the same number of control potato tubers (of the same cultivar as the treated potato tubers) that were not contacted with a sprouting inhibitor; and/or (b) the average rate of growth of stems growing from a defined number of potato tubers contacted with a chemical agent in accordance with the present invention is less than the average rate of growth of stems growing from the same number of control potato tubers (of the same cultivar as the treated potato tubers) that were not contacted with a sprouting inhibitor. Control potato tubers are treated identically to potato tubers contacted with a chemical agent in accordance with the present invention, except as otherwise described.

In accordance with the foregoing, in one aspect, the present invention provides methods for treating potato tubers, the methods each comprising the step of contacting a potato tuber with an amount of a chemical agent that includes at least one aliphatic carbonyl compound selected from the group consisting of a $C_3$ to $C_{14}$, $\alpha,\beta$ unsaturated aliphatic aldehyde and a $C_4$ to $C_{14}$, $\alpha,\beta$ unsaturated aliphatic ketone, wherein the amount of the chemical agent is effective to inhibit potato tuber sprouting.

Some aldehydes useful in the practice of the present invention are defined by formula I, and some ketones useful in the practice of the present invention are defined by formula II:

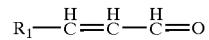

Formula I

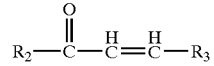

Formula II wherein:
the aliphatic aldehyde of formula I is $C_3$ to $C_{14}$;
the aliphatic ketone of formula II is $C_4$ to $C_{14}$;
$R_1$ is H or branched or unbranched, substituted or unsubstituted $C_1$–$C_{11}$ lower alkyl, or branched or unbranched, substituted or unsubstituted $C_1$–$C_{11}$ lower alkenyl;
$R_2$ is branched or unbranched, substituted or unsubstituted $C_1$–$C_{11}$ lower alkyl, or branched or unbranched, substituted or unsubstituted $C_1$–$C_{11}$ lower alkenyl; and
$R_3$ is H or branched or unbranched, substituted or unsubstituted $C_1$–$C_{10}$ lower alkyl, or branched or unbranched, substituted or unsubstituted $C_1$–$C_{10}$ lower alkenyl.

"Substituted" refers to the replacement of hydrogen with a monovalent or divalent radical. Suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like.

Some chemical agents useful in the practice of the methods of the invention consist essentially of a single aliphatic carbonyl compound defined by formula I or by formula II. Some chemical agents useful in the practice of the methods of the invention include two or more aliphatic carbonyl compounds defined by formula I and/or by formula II. Some chemical agents useful in the practice of the methods of the invention include one or more aliphatic carbonyl compounds defined by formula I and/or by formula II, but do not include a chemical compound not encompassed by formula I or formula II. Non-limiting examples of useful aliphatic aldehydes defined by formula I include: trans-2-pentenal; trans-2-hexenal; trans-2-heptenal; trans-2-octenal; trans-2-nonenal; trans-2-decenal; trans-2-undecenal; trans-2-dodecenal; trans-2,4,-nonadienal; trans-2, cis-6-nonadienal; trans-3-nonen-2-one. Some chemical agents useful in the practice of the methods of the invention include at least one aliphatic carbonyl compound defined by formula I or by formula II, and also include at least one other compound that possesses the ability to inhibit potato tuber sprouting (e.g., chlorpropham, maleic hydrazide, diisopropylnaphthalene, dimethylnaphthalene, carvone, eugenol, benzothiazide, ethylene, aromatic acids (e.g., anisic acid, coumaric acid, gallic acid), rape oil methyl ester, medium and long-chain alcohols, jasmonates, aromatic aldehydes (e.g., benzaldehyde, salicaldehyde, cinnamaldehyde, hydrocinnamaldehyde, cuminaldehyde, thymol), monoterpenes (e.g., cineole, fenchone, menthol), and essential oils (e.g., mint oils)).

In the practice of the methods of the invention the chemical agent is applied after the potato tubers have been harvested, but typically not later than the onset of sprouting. Thus, in some embodiments of the methods of the invention, the chemical agent is applied to the tubers within one, two, three, four five, six, seven or eight weeks after the tubers are harvested. Typically, the chemical agent is applied before the end of the natural dormancy period of the harvested potato tubers, i.e., before the buds on the potato tubers have begun to sprout. Preferably the chemical agent is applied as close to the end of the natural dormancy period as is practical. The duration of the natural dormancy period is known to those of skill in the art and varies between potato cultivars, and depends on such factors as the physiology and condition of the tubers at harvest, and the storage temperature. For example, Table 1 shows estimates (in days) of the natural dormancy period of specific potato cultivars stored at specified temperatures.

TABLE 1

| Potato cultivar | Dormancy period when stored at 48° F. | Dormancy period when stored at 45° F. |
| --- | --- | --- |
| Russet Burbank | ~130 days | ~140 days |
| Ranger Russet | ~70 days | ~90 days |
| Umatilla Russet | ~110 days | ~125 days |
| Gem Russet | ~120 days | ~135 days |

If potatoes are subject to reconditioning, the chemical agent is typically applied at the beginning of the reconditioning period. Thus, in some embodiments of the invention, the chemical agent is applied one, two, three, four or five weeks before potato tubers are processed to make french fries or potato chips. In the practice of the methods of the invention, the chemical agent may be applied to the potato tubers on more than one occasion (e.g., at least twice) during the storage period.

Typically the chemical agent is applied simultaneously, or substantially simultaneously, to numerous, harvested, potato tubers. Potatoes may be stored in bulk storage sheds designed to hold anywhere from 5000 to 25000 tons. The sheds are designed to precisely control ventilation through the bulk pile (which may be about twenty five feet deep) along with temperature and relative humidity. Temperature is controlled by ventilation with outside air through air washers which also raises the humidity. For example, the chemical agent can be volatilized at high temperature and applied as a thermal fog into the storage ventilation system that circulates air through the potato pile, from bottom to top. The storage sheds are generally closed tight after fogging, and the air may be circulated internally through the pile for several hours after application of the chemical agent. Again by way of example, the chemical agent can also be atomized and introduced into the ventilation system of the storage sheds. Drenches or dips can also be used to apply the chemical agent. The chemical agent can also be impregnated on filters, or other inert materials, to facilitate slow release over time through the ventilation system of the storage sheds. The chemical agent can also be applied as an emulsifiable concentrate for spraying onto fresh market potatoes as they go through sorting and packing lines prior to bagging.

The amount of chemical agent that is applied to the potato tubers is effective to inhibit sprouting of the tubers. In some embodiments of the methods of the invention, sprouting is inhibited by at least 25%. In some embodiments of the methods of the invention, sprouting is inhibited by at least 50%. In some embodiments of the methods of the invention, sprouting is inhibited by at least 75%. In some embodiments of the methods of the invention, sprouting is inhibited by at least 90%. In some embodiments of the methods of the invention, sprouting is inhibited by at least 95%. In some embodiments of the methods of the invention, sprouting is inhibited by 100%.

The amount of chemical agent that is effective to inhibit sprouting of the potato tubers depends on such factors as the composition of the chemical agent and the potato cultivar being treated. In some embodiments of the methods of the invention, the chemical agent is applied to the potato tubers in an amount sufficient to provide a dosage of the at least one carbonyl compound of from 0.001 mmol/kg potato tubers to 100.0 mmol/kg potato tubers. In some embodiments of the methods of the invention, the chemical agent is applied to the potato tubers in an amount sufficient to provide a dosage of the at least one carbonyl compound of from 0.1 mmol/kg potato tubers to 5.0 mmol/kg potato tubers. In some embodiments of the methods of the invention, the at least one carbonyl compound is a $C_8$ or $C_9$ aliphatic carbonyl compound, and the chemical agent is applied to the potato tubers in an amount sufficient to provide a dosage of the $C_8$ or $C_9$ aliphatic carbonyl compound of from 0.5 mmol/kg potato tubers to 1.0 mmol/kg potato tubers. In some embodiments of the methods of the invention, the at least one carbonyl compound is a $C_7$ aliphatic carbonyl compound, and the chemical agent is applied to the potato tubers in an amount sufficient to provide a dosage of the $C_7$ aliphatic carbonyl compound of from 0.5 mmol/kg potato tubers to 1.5 mmol/kg potato tubers. In some embodiments of the methods of the invention, the at least one carbonyl compound is a $C_6$ aliphatic carbonyl compound, and the chemical agent is applied to the potato tubers in an amount sufficient to provide a dosage of the $C_6$ aliphatic carbonyl compound of from 0.5 mmol/kg potato tubers to 3.0 mmol/kg potato tubers.

In this regard, when the chemical agent includes more than one α,β unsaturated aliphatic aldehyde and/or α,β unsaturated aliphatic ketone, the stated dosage refers to the combined amount of the aldehyde(s) and/or ketone(s).

The methods of the present invention are applicable to any potato cultivar including, but not limited to, Russet Burbank, Ranger Russet, Umatilla Russet, Shepody, Norkotah Russet, Yukon Gold, Norchip, Gem Russet, Atlantic, Chipeta, Snowden, and Dark Red Norland.

The following examples merely illustrate the best mode now contemplated for practicing the invention, but should not be construed to limit the invention. All literature citations herein are expressly incorporated by reference.

EXAMPLE 1

This Example shows that trans-2-hexenal inhibits potato tuber sprouting.

Methods: Desiree potatoes were produced in research plots at the Edmonton Research Station, University of Alberta in 1999. The tubers were harvested in September, washed, transported to Washington State University and placed in 4° C. storage in late October. Tubers, selected for uniform size, were taken from the storage area for the experiment in June. The 9-month-old tubers were fully emerged from dormancy after this prolonged storage interval; however, no sprout growth had occurred at the low storage temperature.

The tubers were washed, air-dried, and evenly divided between two 9.2 liter (L) glass desiccators (8 tubers per desiccator). Trans-2-hexenal (200 μL) was pipetted into a 50 milliliter (mL) beaker that was placed inside one of the desiccators. The other desiccator served as control. Both desiccators were closed and the tubers were incubated in the two atmospheres for 32 hours. The desiccators were then opened, an additional 1000 μL of trans-2-hexenal was added to the beaker, and the desiccators were closed for an additional 24 hours. One tuber from each chamber was sampled for trans-2-hexenal content at the end of the 56 hour treatment interval. The treated tubers were then planted in a peat/perlite/soil mix in 15-cm-diameter pots and placed in a greenhouse with no supplemental lighting at 21° C.

The experiment was set up in a randomized complete block design with treatments (2 lines×2 [hexenal]) arranged factorially. Time to plant emergence was recorded and plants were harvested 21 days after planting. Plants were separated into various components (e.g., stems, leaves) at harvest and the effects of trans-2-hexenal on plant morphology were assessed.

Results: as shown in FIGS. 1A–F, trans-2-hexenal clearly inhibited sprouting, and thus plant emergence, and plant growth from potato tubers.

EXAMPLE 2

This Example shows the effect of cultivar identity and tuber exposure time on inhibition of potato tuber sprouting by trans-2-hexenal.

Methods: Ten-month-old Ranger Russet, Umatilla and Russet Burbank seed-tubers were taken from 4° C. storage and treated with trans-2-hexenal in 9.2-L glass desiccators as described in Example 1. The tubers were exposed to trans-2-hexenal for 0, 12 and 24 hours at 23° C. at a concentration of 4.7 mmol/kg potato tubers. Regardless of exposure time, all tubers remained enclosed in the chambers for the entire 24 hour period. This was accomplished by introducing the trans-2-hexenal at zero-time (into the 24 hour treatment desiccator) and after 12 hour incubation (into the 12 hour treatment desiccator) through a septum in the top of the closed desiccator. The treated tubers were planted into moistened peat/perlite/soil potting mix and placed in the dark at 24° C. to stimulate sprouting. The experiment was set up in a randomized complete block design (5 replicates) with treatments (3 cultivars×3 exposure times) arranged factorially. Effects of trans-2-hexenal exposure and cultivar on etiolated sprout development and tuber quality were assessed 25 days after removal from the 4° C. storage.

Results: Tubers were photographed after 14 days and at harvest (25 days) to document effects on sprout development. As shown in Table 1, while cultivar influenced the degree of sprouting, trans-2-hexenal effectively inhibited sprout development from all cultivars. As shown in Table 1, trans-2-hexenal damage to the periderm (skin) was dose and cultivar dependent. The damage appeared as small pits of sunken tissue encompassing some of the lenticels. The severity of pitting increased with time of exposure to trans-2-hexenal and Russet Burbank tubers were more resistant than Umatilla and Ranger Russet tubers. Soft rot lesions were also apparent on trans-2-hexenal-treated tubers; however, this was more a consequence of tubers being buried in moist medium for 25 days without sprouting than to a direct effect of trans-2-hexenal on susceptibility to the soft rot organism. In fact, trans-2-hexenal has been shown to inhibit bacterial growth on other harvested plant commodities (Corbo et al., *J. Agric. Food Chem.* 48:2401–2408 (2000); Archbold et al., *HortScience* 34:705–707 (1999)).

As shown in Table 2, the concentrations of reducing sugars and sucrose were substantially lower in trans-2-hexenal-treated Russet Burbank tubers compared with sprouted controls, supporting the use of the aldehyde as a reconditioning agent. Low sugars are a requisite to maintaining processing quality.

TABLE 2

| Cultivar | Hexenal Exposure (4.7 mmol/ kg potato tubers) (h) | Sprout Fresh Weight (g/tuber) | Average Sprout Length (cm/tuber) | External Pit Rating (1–4 scale)* | Soft Rot Lesions (no/tuber) | Soluble Carbohydrates | | | |
|---|---|---|---|---|---|---|---|---|---|
| | | | | | | Suc | Glu | Fru | Glu + Fru |
| | | | | | | (mg/g dry wt.) | | | |
| Umatilla | 0 | 164 | 39.1 | 1.0 | 0 | — | — | — | — |
| | 12 | 0 | 0 | 3.7 | 2.2 | — | — | — | — |
| | 24 | 0 | 0 | 4.0 | 2.6 | — | — | — | — |
| Ranger Russet | 0 | 125 | 46.7 | 1.0 | 0 | — | — | — | — |
| | 12 | 0 | 0 | 3.1 | 1.0 | — | — | — | — |
| | 24 | 0 | 0 | 3.7 | 1.2 | — | — | — | — |

TABLE 2-continued

| Cultivar | Hexenal Exposure (4.7 mmol/ kg potato tubers) (h) | Sprout Fresh Weight (g/tuber) | Average Sprout Length (cm/tuber) | External Pit Rating (1–4 scale)* | Soft Rot Lesions (no/tuber) | Soluble Carbohydrates (mg/g dry wt.) | | | |
|---|---|---|---|---|---|---|---|---|---|
| | | | | | | Suc | Glu | Fru | Glu + Fru |
| Russet Burbank | 0 | 121 | 47.2 | 1.0 | 0 | 12.7 | 70.9 | 73.8 | 145 |
| | 12 | 0 | 0 | 1.8 | 0.6 | 6.30 | 19.0 | 19.5 | 38.5 |
| | 24 | 0 | 0 | 2.2 | 0.4 | 6.28 | 16.5 | 17.8 | 34.3 |
| U/R, B | | 0.01 | 0.01 | — | — | — | — | — | — |
| R/B | | ns | ns | — | — | — | — | — | — |
| U, R/B | | — | — | 0.01 | 0.05 | — | — | — | — |
| U/R | | — | — | 0.05 | 0.05 | — | — | — | — |
| Exposure | | 0.01 | 0.01 | 0.01 | 0.01 | 0.05 | 0.01 | 0.01 | 0.01 |
| $E_{LT}$ | | — | — | 0.01 | 0.01 | 0.05 | 0.01 | 0.01 | 0.01 |
| $E_{QT}$ | | — | — | 0.01 | ns | ns | 0.01 | 0.01 | 0.01 |
| $E_{LT}$ × U/R, B | | — | — | — | — | — | — | — | — |
| $E_{QT}$ × U/R, B | | — | — | — | — | — | — | — | — |
| $E_{LT}$ × R/B | | — | — | — | — | — | — | — | — |
| $E_{QT}$ × R/B | | — | — | — | — | — | — | — | — |
| $E_{LT}$ × U, R/B | | — | — | 0.01 | 0.05 | — | — | — | — |
| $E_{QT}$ × U, R/B | | — | — | 0.05 | ns | — | — | — | — |
| $E_{LT}$ × U/R | | — | — | ns | ns | — | — | — | — |
| $E_{QT}$ × U/R | | — | — | ns | ns | — | — | — | — |

*1 = no pits; 2 = widely spaced and/or very small (<10%) pitted surface area; 3 = pitted surface area equal to 10–50% of tuber surface; 4 = tuber surface uniformly pitted on all sides (>50% pitted).

The following abbreviations are used in Table 2: Umatilla (U); Ranger Russett (R); Russett Burbank (B); sucrose (suc); glucose (glu); fructose (fru); exposure time linear trend ($E_{LT}$); exposure time quadratic trend ($E_{QT}$); centimeter (cm); gram (g); hour (h); number (no.); and milligram (mg).

EXAMPLE 3

This Example describes the effect of trans-2-hexenal on potato tuber respiration. Dormant tubers have a relatively low respiration rate, which is a desirable characteristic for prolonged storage. Low respiration conserves dry matter, minimizes vital heat, prevents $CO_2$ buildup, and slows maturation and premature aging of tubers.

Methods: Eleven-month-old Russet Burbank seed-tubers were taken from a 4° C. storage area and treated with 250 μL of trans-2-hexenal in a 9.2 liter (L) glass desiccator (0.96 mmol/kg potato tubers) for 12 hours at 23° C. The trans-2-hexenal was pipetted onto Whatman #1 filter paper in a glass petri dish (5.5 cm diameter) inside the desiccator. Control tubers were enclosed in a desiccator without trans-2-hexenal. Following treatment, the tubers were enclosed in 1 L nalgene chambers (3 tubers per chamber) that were placed at 15° C. A continuous airflow (approximately 80 mL/min; 21% $O_2$, 79% $N_2$) was established around the tubers through inlet and outlet ports in the lid of each chamber. Respiration rates were determined at four hour intervals over a 28 day storage period by quantifying $CO_2$ in the outflow from each chamber with a LI-COR model 6262 infra-red gas analyzer (LI-COR Inc., Lincoln Nebr.). The experiment was set up in a randomized complete block design (5 replicates) with two treatments (control and trans-2-hexenal-treated). The effect of trans-2-hexenal exposure on the development of etiolated sprouts was assessed 28 days after removal from the 4° C. storage.

Results: The respiration rate of trans-2-hexenal-treated tubers was 38% greater (P>0.05) than untreated tubers immediately following the 12 hour treatment period. Control tubers maintained a relatively constant rate of respiration (approx. 7.6 mL $CO_2$/kg/h) over the initial 64 hours of storage at 15° C. Respiration of trans-2-hexenal-treated tubers declined rapidly over the initial 10 hours of storage, reaching a level that was equal to the untreated tubers by 32 hours after treatment. Control and trans-2-hexenal-treated tubers maintained equal rates of respiration that declined steadily from 32 to 150 hours. Respiration rate of control tubers then gradually increased over the remainder of the 27 day storage interval concomitant with sprouting.

In contrast, respiration of trans-2-hexenal-treated tubers continued to fall and was 2.5-fold lower than control tubers by the end of the study. As shown in Table 3, consistent with previous studies, trans-2-hexenal inhibited sprouting.

TABLE 3

| | Tuber Treatment | |
|---|---|---|
| Variable | Untreated | trans-2-Hexenal (0.96 mmol/kg) |
| Sprout fresh wt (g/tuber) | 4.0 | 0** |
| Average sprout length (cm/tuber) | 5.4 | 0** |
| Tuber external pit rating | 1.0 | 2.2** |
| Tuber fresh wt loss (g/tuber) | 31.0 | 11.8** |

**Significantly different from untreated control at P < 0.01.

The initially-high rate of respiration in hexenal-treated tubers may be beneficial to quality, stimulating catabolism of excess reducing sugars and thus reconditioning the tubers.

EXAMPLE 4

This Example compares the abilities of trans-2-hexenal, trans-2-heptenal and trans-2 octenal to inhibit sprouting in potato tubers.

Methods: Eleven-month-old Russet Burbank seed tubers were taken from a 4° C. storage area and exposed to trans-2-hexenal (0.6–4.3 mmol/kg), trans-2-heptenal (0.6–3.8 mmol/kg) and trans-2-octenal (0.5–2.5 mmol/kg) vapors separately in 3.9 L glass containers for 12 hours at 23° C. The aldehydes were applied to filter paper inside petri dishes within each jar. Control tubers were enclosed in a glass container without any aldehyde. Sprouts were 'peeping' (approximately 3 mm in length) at the time of treatment. Following treatment, tubers were placed at 18° C. (95% relative humidity) in the dark to sprout for 26 days. The experiment was set up in a randomized complete block design (5 replicates) with chemicals and concentrations arranged factorially. Effects of the aliphatic aldehydes on the development of etiolated sprouts were documented at 20 days (photographically) and 26 days of sprouting.

Results: All of the aliphatic aldehydes inhibited sprouting at all concentrations tested. Comparisons among aldehydes at a particular concentration were not possible in this study, as molar concentrations in the vapor phases were not exactly equivalent (due to differences in vapor pressures that were not considered in this study).

Effects of the aldehydes on sprout development and tuber quality at the end of the study (26 days) are reported in Table 4.

TABLE 4

| Treatment | Aldehyde Concentration (mmol/kg) | Sprout Fresh Weight (g/tuber) | Average Sprout Length (cm/tuber) | External Pit Rating (1–4 scale)* |
|---|---|---|---|---|
| Control | — | 7.70** | 8.8** | 1.0 |
| trans-2-Hexenal | 0.63 | 0.04 | 0.2 | 1.4 |
|  | 1.33 | 0 | 0 | 2.0 |
|  | 2.06 | 0 | 0 | 2.6 |
|  | 2.50 | 0 | 0 | 3.5 |
|  | 4.34 | 0 | 0 | 2.8 |
| trans-2-Heptenal | 0.56 | 0.01 | 0.2 | 1.0 |
|  | 1.11 | 0 | 0 | 1.6 |
|  | 1.69 | 0 | 0 | 1.4 |
|  | 2.16 | 0 | 0 | 2.3 |
|  | 3.85 | 0 | 0 | 2.5 |
| trans-2-Octenal | 0.50 | 0 | 0 | 1.0 |
|  | 0.97 | 0 | 0 | 1.0 |
|  | 1.44 | 0 | 0 | 1.6 |
|  | 1.93 | 0.10 | 0.2 | 1.3 |
|  | 2.48 | 0.13 | 0.2 | 1.3 |

*1 = no pits; 2 = widely spaced and/or very small (<10%) pitted surface area; 3 = pitted surface area equal to 10–50% of tuber surface; 4 = tuber surface uniformly pitted on all sides (>50% pitted).
**Significantly different from all other treatments at P > 0.01.

External pitting of trans-2-hexenal-treated tubers was minimal at the lowest concentration, but increased significantly with concentration. Moreover, the extent of aldehyde-induced, external pitting of the periderm decreased as carbon number increased (hexenal>heptenal>octenal).

EXAMPLE 5

This Example compares the efficacy of different concentrations of $C_5$ to $C_9$ trans-2 aldehydes at inhibiting sprouting of Russet Burbank and Ranger Russet potato tubers over a prolonged storage period.

Methods: Four-month-old Russet Burbank and Ranger Russet seed-tubers were taken from a 4° C. storage area and treated (Jan. 10, 2001) separately with 0, 0.5, 0.75 and 1.0 mmol/kg tuber of trans-2-pentenal, trans-2-hexenal, trans-2-heptenal, trans-2-octenal, and trans-2-nonenal in 3.9 L glass jars. The volume of inhibitor required to achieve the above rates was pipetted onto filter paper discs inside the lids of each jar. The concentration of inhibitors in the headspace of the jars was equal at 0.16 mmol/L. The tubers were enclosed in the jars and thus exposed to inhibitor vapor for 24 hours at 23° C. Control tubers were enclosed in a glass jar without any aldehyde. Following treatment, tubers were removed from the jars and placed at 8° C. (46° F.) (95% relative humidity) in the dark to sprout for 120 days (17 weeks). The experiment was set up in a randomized complete block design (5 replicates) with chemicals and concentrations arranged factorially. Effects of the aliphatic aldehydes on the development of etiolated sprouts were documented photographically and quantitatively (sprout number and fresh weight) after 120 days of storage.

Results: Comparisons between aldehydes for their ability to inhibit sprouting is possible in this study as aldehydes were applied at equivalent molar concentrations on a tuber weight (kg) and headspace basis. The degree of inhibition of sprouting after 17 weeks (4 months) of storage at 8° C. depended on aldehyde and concentration (see FIGS. 2A–D).

Trans-2-octenal and trans-2-nonenal totally inhibited sprout development at all concentrations. Moreover, these two aldehydes did not induce external pitting damage to the periderm relative to that induced by the $C_5$ to $C_7$ aldehydes. $C_5$, $C_6$ and $C_7$ aldehydes inhibited sprouting in a concentration-dependent manner and, in general, the degree of inhibition at a particular concentration increased with increased carbon chain length of the aldehyde ($C_8$ and $C_9$>$C_7$>$C_6$>$C_5$).

EXAMPLE 6

This Example shows the efficacy of trans-2-nonenal as a sprout inhibitor to facilitate reconditioning, and thus improve processing quality of tubers that had developed high sugar levels during storage at low temperatures.

Methods: Russet Burbank tubers were stored at 7° C. (44° F.) from harvest Oct. 29, 2000 to Jan. 26, 2001. The tubers were transferred to 4° C. (40° F.) on Jan. 26, 2001, until treatment on Apr. 2, 2001. Tubers were treated with 0.45 mmol/kg trans-2-nonenal in 9.2 L glass desiccators for 17 hours at 23° C. Following treatment, the tubers were placed at 14° C. (57° F.) to recondition for 0, 1, 2, 3 and 4 weeks. French fries were processed from the reconditioned tubers by frying longitudinal slices (⅜" thick×1⅛" wide) of potato tuber in 375° F. (190° C.) oil for 3.5 minutes. Fry darkness of the apical and basal ends of the fries was quantified with a photovolt reflectance meter within three minutes of frying. A high reflectance reading (photovolt unit) indicates light fry color due to a relatively low sugar level and thus a high-quality processed product. Conversely, a low reflectance reading indicates dark fry color due to high sugar content, resulting in low processing quality. Treatments (plus and minus trans-2-nonenal; 5 reconditioning times) were arranged factorially in a randomized complete block design with 12 replicates. Sprout fresh weight and fry color were recorded.

Figure 3:
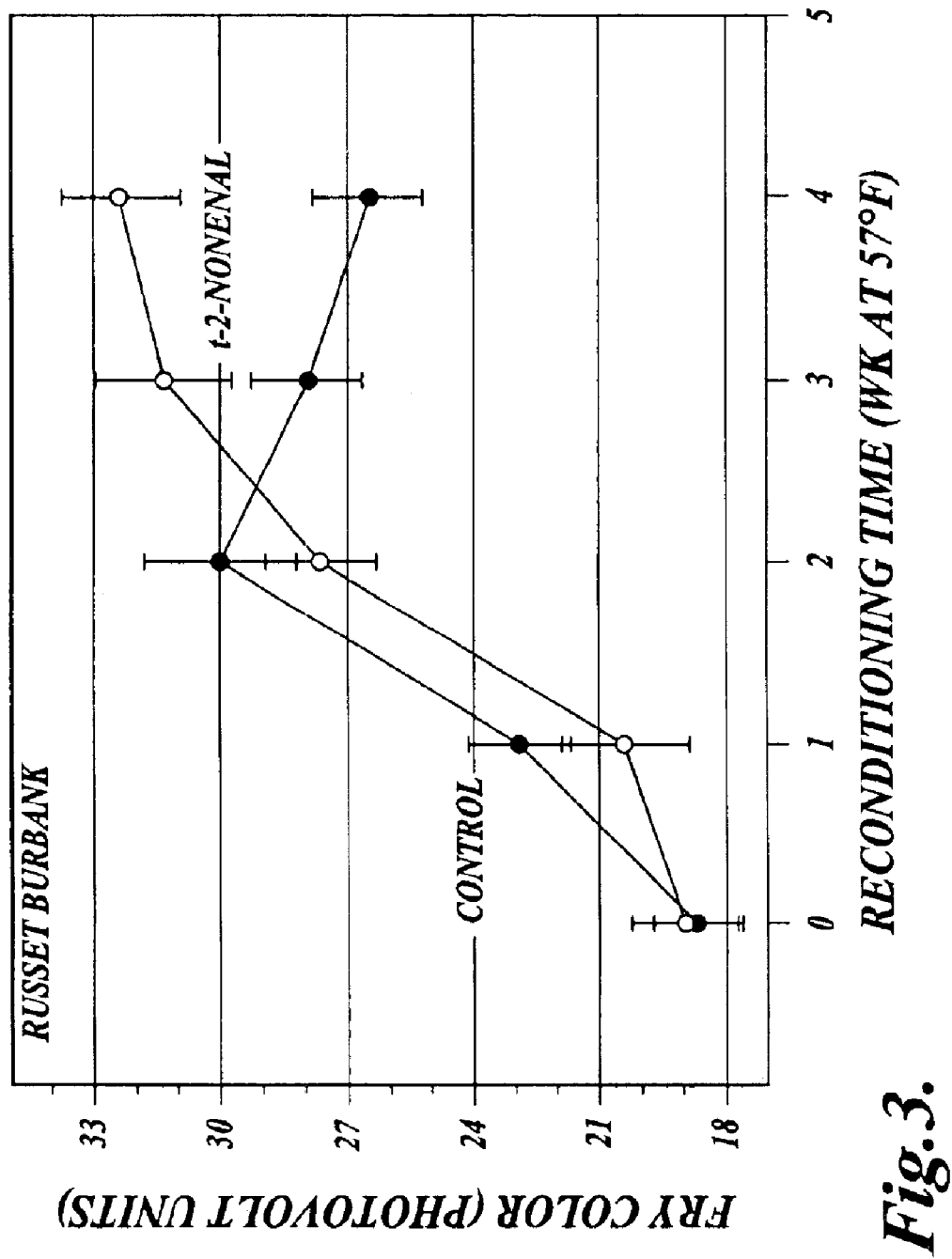
FIG. 3 shows the effects of trans-2-nonenal on reconditioning of Russet Burbank potatoes. Seven-month-old tubers from 4° C. (40° F.) storage were treated with 0.45 mmol/kg trans-2-nonenal for 17 hours at 23° C. The tubers were then placed at 14° C. (57° F.) to recondition. French fries were processed from the tubers through four weeks of reconditioning. Fry color (lightness or darkness) was quantified with a photovolt reflectance meter. High photovolt values indicate light-colored fries (high processing quality). Low photovolt values indicate low-quality, dark-colored fries.

Results: Color of fries from unconditioned (i.e., zero reconditioning) control and trans-2-nonenal-treated tubers was unacceptably dark following low temperature storage (see FIG. 3). Fry color became progressively lighter (higher photovolt units) as reconditioning time at 57° F. increased, indicating a significant improvement in processing quality of both control and trans-2-nonenal-treated tubers. The processing quality of control tubers, however, declined from 2 to 4 weeks of reconditioning, while that of trans-2-nonenal-treated tubers continued to increase (see FIG. 3). These effects were attributable to differences in sprout development over the four week reconditioning period at 57° F. Control tubers produced about four fold more sprouts (50.4 g fresh weight/12 tubers vs. 13.5 g fresh weight/12 tubers) than trans-2-nonenal-treated tubers at four weeks of reconditioning. Trans-2-nonenal-induced inhibition of sprouting thus facilitated more extensive reconditioning and improvement of processing quality of tubers over the four week interval.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for inhibiting sprouting of potato tubers, the method comprising the step of contacting a potato tuber with an amount of a chemical agent comprising at least one aliphatic carbonyl compound selected from the group consisting of a $C_3$ to $C_{14}$, $\alpha,\beta$ unsaturated aliphatic aldehyde and a $C_4$ to $C_{14}$, $\alpha,\beta$ unsaturated aliphatic ketone, wherein the amount of the chemical agent is effective to inhibit potato tuber sprouting.

2. The method of claim 1 wherein the aliphatic aldehyde is defined by formula I and the aliphatic ketone is defined by formula II:
wherein:

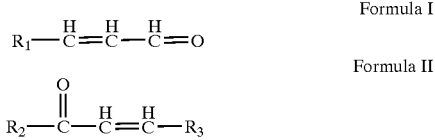

Formula I

Formula II the aliphatic aldehyde of formula I is $C_3$ to $C_{14}$;
the aliphatic ketone of formula II is $C_4$ to $C_{14}$;
$R_1$ is H or branched or unbranched, substituted or unsubstituted $C_1$–$C_{11}$ lower alkyl, or branched or unbranched, substituted or unsubstituted $C_1$–$C_{11}$ lower alkenyl;
$R_2$ is branched or unbranched, substituted or unsubstituted $C_1$–$C_{11}$ lower alkyl, or branched or unbranched, substituted or unsubstituted $C_1$–$C_{11}$ lower alkenyl; and
$R_3$ is H or branched or unbranched, substituted or unsubstituted $C_1$–$C_{10}$ lower alkyl, or branched or unbranched, substituted or unsubstituted $C_1$–$C_{10}$ lower alkenyl.

3. The method of claim 2 wherein the chemical agent comprises an aliphatic aldehyde defined by formula I.

4. The method of claim 3 wherein the aliphatic aldehyde is selected from the group consisting of trans-2-pentenal; trans-2-hexenal; trans-2-heptenal; trans-2-octenal; trans-2-nonenal; trans-2-decenal; trans-2-undecenal; trans-2-dodecenal; trans-2,4,-nonadienal; trans-2, cis-6-nonadienal; and trans-3-nonen-2-one.

5. The method of claim 4 wherein the aliphatic aldehyde is trans-2-pentenal.

6. The method of claim 4 wherein the aliphatic aldehyde is trans-2-hexenal.

7. The method of claim 4 wherein the aliphatic aldehyde is trans-2-heptenal.

8. The method of claim 4 wherein the aliphatic aldehyde is trans-2-octenal.

9. The method of claim 4 wherein the aliphatic aldehyde is trans-2-nonenal.

10. The method of claim 4 wherein the aliphatic aldehyde is trans-2-decenal.

11. The method of claim 4 wherein the aliphatic aldehyde is trans-2-undecenal.

12. The method of claim 4 wherein the aliphatic aldehyde is trans-2-dodecenal.

13. The method of claim 4 wherein the aliphatic aldehyde is trans-2,4,-nonadienal.

14. The method of claim 4 wherein the aliphatic aldehyde is trans-2, cis-6-nonadienal.

15. The method of claim 4 wherein the aliphatic aldehyde is trans-3-nonen-2-one.

16. The method of claim 2 wherein the chemical agent comprises an aliphatic ketone defined by formula II.

17. The method of claim 1 wherein the amount of chemical agent is sufficient to provide a dosage of the at least one carbonyl compound of from 0.001 mmol/kg potato tubers to 100 mmol/kg potato tubers.

18. The method of claim 1 wherein the amount of chemical agent is sufficient to provide a dosage of the at least one carbonyl compound of from 0.1 mmol/kg potato tubers to 5.0 mmol/kg potato tubers.

19. The method of claim 1 wherein the chemical agent comprises a $C_3$ to $C_{14}$, $\alpha,\beta$ unsaturated aliphatic aldehyde, and the amount of chemical agent is sufficient to provide a dosage of the aliphatic aldehyde of from 0.001 mmol/kg potato tubers to 100 mmol/kg potato tubers.

20. The method of claim 1 wherein the chemical agent comprises a $C_3$ to $C_{14}$, $\alpha,\beta$ unsaturated aliphatic aldehyde, and the amount of chemical agent is sufficient to provide a dosage of the aliphatic aldehyde of from 0.1 mmol/kg potato tubers to 5.0 mmol/kg potato tubers.

21. The method of claim 20 wherein the aliphatic aldehyde is $C_8$ or $C_9$ and the amount of chemical agent is sufficient to provide a dosage of the aliphatic aldehyde of from 0.5 mmol/kg potato tubers to 1.0 mmol/kg potato tubers.

22. The method of claim 20 wherein the aliphatic aldehyde is $C_7$ and the amount of chemical agent is sufficient to provide a dosage of the aliphatic aldehyde of from 0.5 mmol/kg potato tubers to 1.5 mmol/kg potato tubers.

23. The method of claim 20 wherein the aliphatic aldehyde is $C_6$ and the amount of chemical agent is sufficient to provide a dosage of the aliphatic aldehyde of from 0.5 mmol/kg potato tubers to 3.0 mmol/kg potato tubers.

24. The method of claim 1 wherein the chemical agent comprises a $C_4$ to $C_{14}$, $\alpha,\beta$ unsaturated aliphatic ketone, and the amount of chemical agent is sufficient to provide a dosage of the aliphatic ketone of from 0.001 mmol/kg potato tubers to 100 mmol/kg potato tubers.

25. The method of claim 24 wherein the amount of chemical agent is sufficient to provide a dosage of the aliphatic ketone of from 0.1 mmol/kg potato tubers to 5.0 mmol/kg potato tubers.

26. The method of claim 24 wherein the aliphatic ketone is $C_8$ or $C_9$ and the amount of chemical agent is sufficient to provide a dosage of the aliphatic ketone of from 0.5 mmol/kg potato tubers to 1.0 mmol/kg potato tubers.

27. The method of claim 24 wherein the aliphatic ketone is $C_7$ and the amount of chemical agent is sufficient to provide a dosage of the aliphatic ketone of from 0.5 mmol/kg potato tubers to 1.5 mmol/kg potato tubers.

28. The method of claim 24 wherein the aliphatic ketone is $C_6$ and the amount of chemical agent is sufficient to provide a dosage of the aliphatic ketone of from 0.5 mmol/kg potato tubers to 3.0 mmol/kg potato tubers.

29. The method of claim 2 wherein the chemical agent consists essentially of an aliphatic aldehyde defined by formula I.

30. The method of claim 2 wherein the chemical agent consists essentially of an aliphatic ketone defined by formula II.

31. The method of claim 1 wherein the potato tuber is from a cultivar selected from the group consisting of Russet Burbank, Ranger Russet, Umatilla Russet, Shepody, Norkotah Russet, Yukon Gold, Norchip, Gem Russet, Atlantic, Chipeta, Snowden, and Dark Red Norland.

32. The method of claim 1 wherein the potato tuber is contacted with the chemical agent during a time period extending from harvest of the tuber to one week prior to utilization by a processor or a consumer.

33. The method of claim 32 wherein the potato tuber is contacted with the chemical agent within one month after harvest.

34. The method of claim 32 wherein the potato tuber is contacted with the chemical agent within two months after harvest.

35. The method of claim 32 wherein the potato tuber is contacted with the chemical agent within one month before utilization by a consumer.

* * * * *